US00PP36137P2

(12) United States Plant Patent
Chaussard

(10) Patent No.: US PP36,137 P2
(45) Date of Patent: Sep. 24, 2024

(54) ***COTINUS* PLANT NAMED 'Mincolem04'**

(50) Latin Name: *Cotinus coggygria*
Varietal Denomination: Mincolem04

(71) Applicant: Pierre Chaussard, Saint Mathurin sur Loire (FR)

(72) Inventor: Pierre Chaussard, Saint Mathurin sur Loire (FR)

(73) Assignee: HORTIVAL DIFFUSION, Beaufort en Anjou (FR)

( * ) Notice: Subject to any disclaimer, the term of this patent is extended or adjusted under 35 U.S.C. 154(b) by 0 days.

(21) Appl. No.: 18/420,714

(22) Filed: Jan. 23, 2024

(30) Foreign Application Priority Data

Apr. 3, 2023 (QZ) ..... PBR 2023/0474

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Cotinus coggygria* named 'Mincolem04' that is characterized by its foliage coloration that is yellow-orange in color for new growth, yellow-lime in spring, becoming more green in summer, and then turning to a blend of yellow, green, orange and red in autumn, its strong stems, its medium to vigorous growth habit, and its erect, well branched plant form.

4 Drawing Sheets

Botanical classification: *Cotinus coggygria.*
Variety denomination: 'Mincolem04'.

CROSS REFERENCE TO A RELATED APPLICATION

This application is related to a European plant breeders' rights application filed on Apr. 3, 2023, application No. 2023/0474. The Applicant received the information for the Plant breeders' rights application directly from the Inventor.

BACKGROUND OF THE INVENTION

The present invention relates to a new and distinct cultivar of *Citinus coggygria* and will be referred to hereafter by its cultivar name, 'Mincolem04'. 'Mincolem04' is a new cultivar of smokebush grown for use as a landscape plant.

The new cultivar of *Cotinus* arose from a breeding program conducted by the Inventor in La Ménitré, France with the goal of developing a new *Cotinus* cultivar with yellow foliage and a strong, erect, and well-branched plant habit. The Inventor made a cross in May of 2009 between unnamed and unpatented proprietary plants of *Citinus coggygria* from the Inventor's breeding program, reference no. 4450 as the female parent and reference no. 11159 as the male parent. The Inventor selected 'Mincolem04' in June of 2014 as a single unique plant amongst the seedlings that resulted from the above cross.

Asexual propagation of the new cultivar was first accomplished by stem cuttings in June 2014 by the Inventor in La Ménitré, Maine et Loire, France. Asexual propagation by stem cuttings has determined the characteristics of the new cultivar are stable and reproduced true to type in successive generations.

SUMMARY OF THE INVENTION

The following traits have been repeatedly observed and represent the characteristics of the new cultivar. These attributes in combination distinguish 'Mincolem04' as a unique cultivar of *Cotinus.*

1. 'Mincolem04' exhibits foliage coloration that is yellow-orange in color for new growth, yellow-lime in spring, becoming more green in summer, and then turning to a blend of yellow, green, orange and red in autumn.
2. 'Mincolem04' exhibits inflorescence that are yellow-pink in color.
3. 'Mincolem04' exhibits strong stems.
4. 'Mincolem04' exhibits a medium to vigorous growth habit.
5. 'Mincolem04' exhibits an erect, well branched plant form.

The female parent of 'Mincolem04' differs from 'Mincolem04' in having more pure yellow foliage color and thinner stems. The male parent of 'Mincolem04' differs from 'Mincolem04' in having foliage that is green in color and a more compact plant habit. 'Mincolem04' can be compared to the *Citinus coggygria* cultivars 'Mincojau3' (U.S. Plant Pat. No. 30,327) and 'Young Lady' (not patented). 'Mincojau3' differs from 'Mincolem04' in having thinner stems, inflorescences that are green in color, a less erect plant habit, a less vigourous growth habit, and foliage that is yellow in summer and turning brown in fall. 'Young Lady' differs from 'Mincolem04' in having thinner stems, foliage that is bluish green in color, and a more floriferous plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include website listings by Pepinieres-minier and Garden.EE.

BRIEF DESCRIPTION OF THE DRAWINGS

The accompanying colored photographs illustrate the overall appearance and distinct characteristics of the new *Cotinus*. The plant in the photographs for FIG. 1, FIG. 2, and FIG. 3 were taken of a 1-year-old plant as grown outdoors in 4-liter containers in La Ménitré, France. The plant in the photograph for FIG. 4 was taken of a 2-year-old plant as grown outdoors in a 10-liter container in La Ménitré, France.

The photograph in FIG. 1 illustrates the overall plant habit and foliage coloration of 'Mincolem04' in summer.

Figure 1:
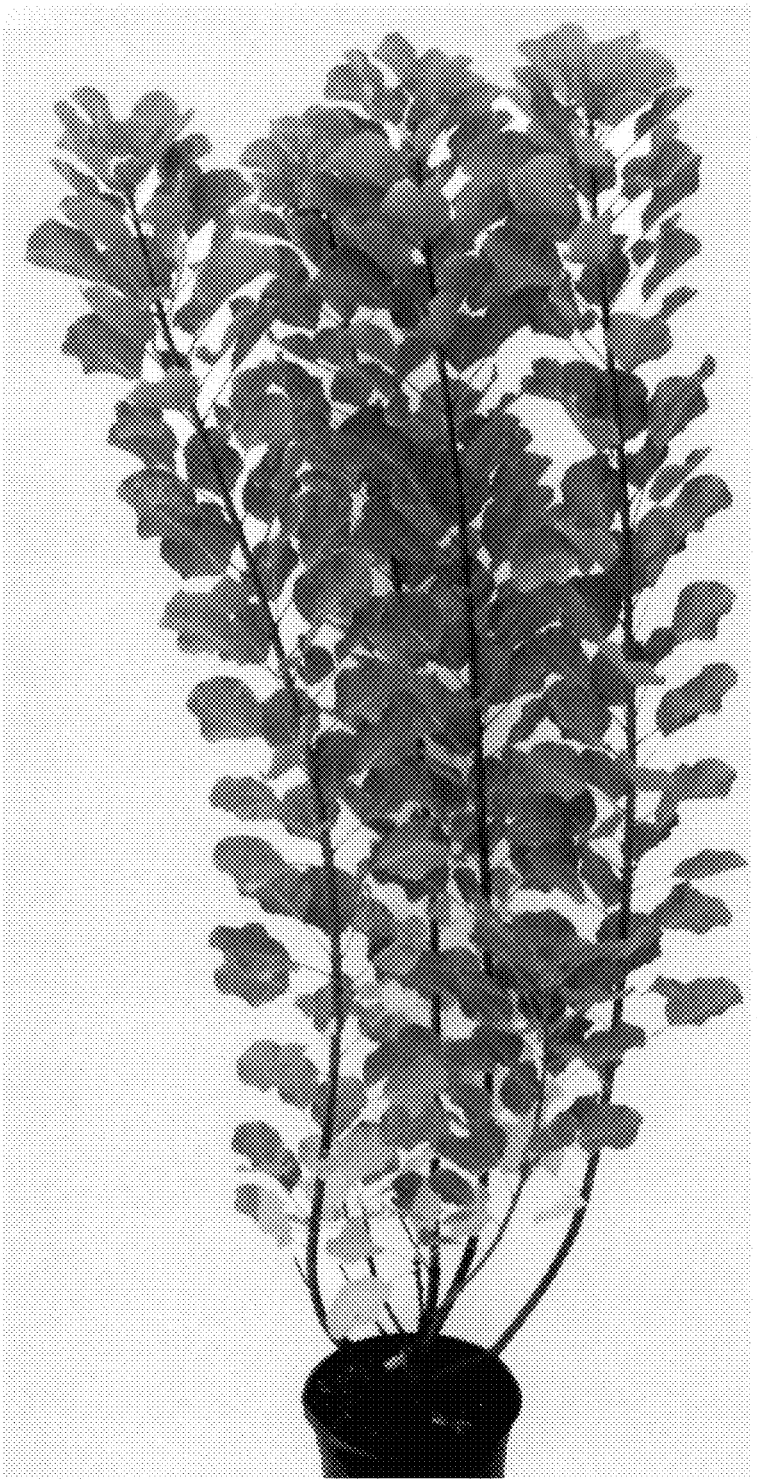
Figure 2:
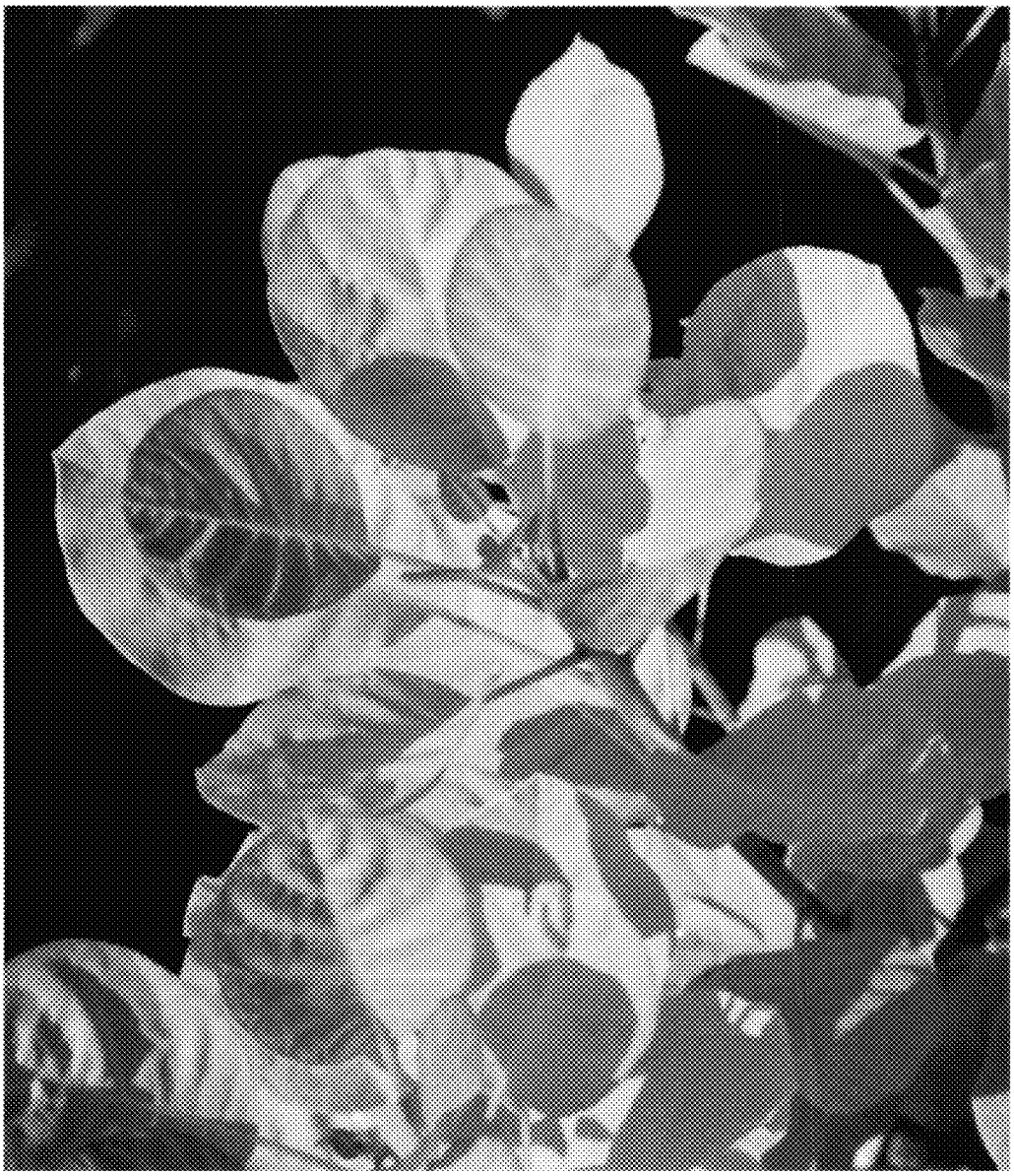

The photograph in FIG. 2 provides a view of the emerging and young foliage in spring of 'Mincolem04'.

Figure 3:
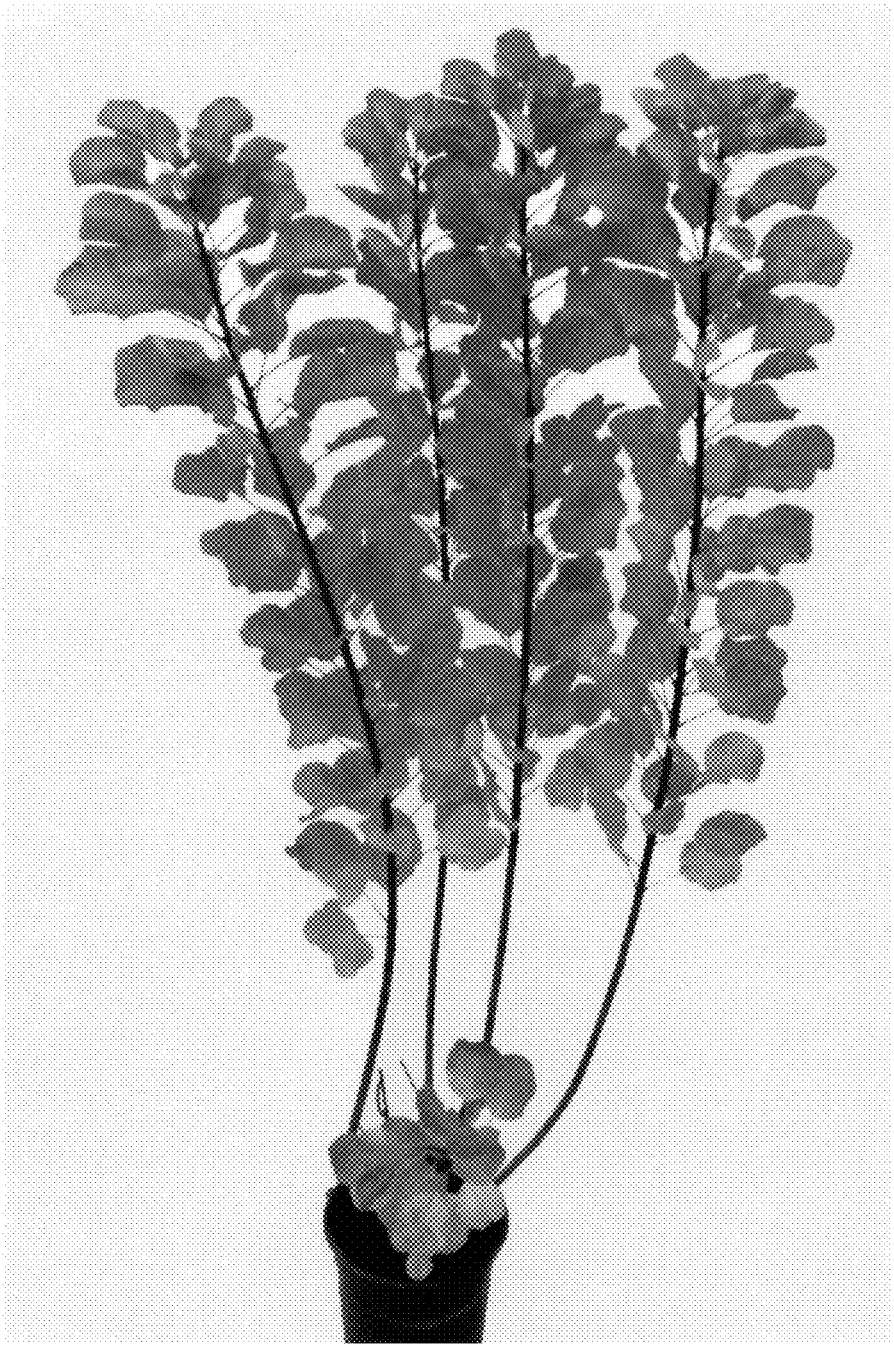

The photograph in FIG. 3 provides a view of the fall foliage in spring of 'Mincolem04'.

Figure 4:
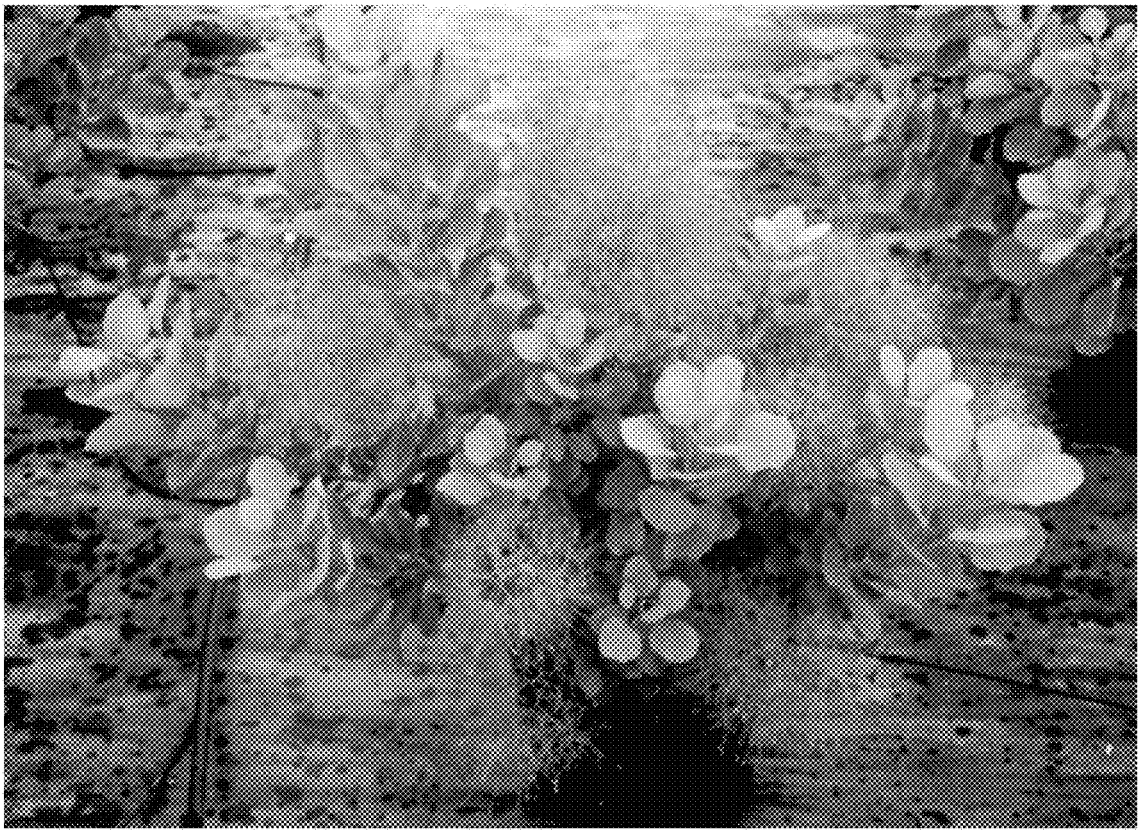

The photograph in FIG. 4 provides a view of a plant of 'Mincolem04' with inflorescences.

The colors in the photographs are as close as possible with the digital photography techniques utilized and the color values cited in the detailed botanical description accurately describe the colors of the new *Cotinus*.

DETAILED BOTANICAL DESCRIPTION

The following is a detailed description of 1-year-old plants of the new cultivar as grown in 2-gallon containers in Cottage Grove, Minnesota. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—True flowers appear in May and inflorescence remains showy for at least a month due to pedicels in France.

*Plant type.*—Deciduous shrub.

*Plant habit.*—Upright, strong stems.

*Height and spread.*—Average of 34 cm in length, 51 cm in width as a one-year-old plant in a container and reaches about 1.8 m in height and 1.5 m in spread as grown n the landscape in France.

*Cold hardiness.*—At least in U.S.D.A. Zone 4.

*Diseases and pests.*—No susceptibility and resistance to diseases or pests has been observed.

*Root description.*—Fibrous and fine, N170A and 200A.

*Propagation.*—Stem cuttings.

*Root development.*—Roots intiate in about 6 weeks and a young rooted plant is produced in about 1 year from a rooted cutting.

*Growth rate.*—Vigorous.

Branch description:

*Branch shape.*—Round.

*Branching.*—1 main branch, average of 6 secondary branches, alternate and whorled.

*Branch color.*—Young; 143A, mature; 144A, older stems; 164A to 164B, bark; 197C and 198D.

*Branch size.*—Main branch; 13 cm in length, 1 cm in diameter, lateral branches; 15 cm in length, 5 mm in diameter.

*Stem surface.*—Young; glossy and glabrous, mature; matte, glabrous, lightly vertically ribbed, and moderately covered with lenticels that are round in shape, 0.4 mm in size, and range in color as the stem ages between 163B and NN155D in color, older wood; slightly sheen, moderately covered with stem scars rounded in shape, 200A in color, moderately covered with lenticels that are round in shape, 0.3 mm in size, NN155D in color, 3 mm in diameter, bark; matte, exfoliating.

*Internode length.*—Average of 1 cm.

Foliage description:

*Leaf shape.*—Ovate.

*Leaf division.*—Simple.

*Leaf base.*—Rounded.

*Leaf apex.*—Obtuse to rounded.

*Leaf venation.*—Pinnate, color: emerging and young; match leaf surface, mature; upper surface 145C, lower surface 145B.

*Leaf margins.*—Entire and slightly undulate.

*Leaf arrangement.*—Alternate and whorled.

*Leaf attachment.*—Petiolate.

*Leaf surface.*—Emerging and young; both surfaces slightly glossy, glabrous, satiny and somewhat translucent, thinner density, mature; both surfaces matte, slightly rugose, glabrous and have a thicker density.

*Leaf size.*—Average of 4 cm in length, 1.7 cm in width.

*Leaf quantity.*—Average of 22 per lateral branch.

*Leaf color.*—Emerging; both surfaces N144A, very lightly flushed 172A, young; both surfaces N144A, mature; upper surface NN137A, lower surface 138A, autumn; both surfaces a blend of 11A, 140B, 154A, 26A, 34A and 46A.

*Leaf fragrance.*—When rubbed, a strong citronella smell.

*Petioles.*—Up to 6 mm in length, 2 mm in width, surfaces are matte and glabrous, color: young; both surfaces 144B, mature; both surfaces 145B, lightly flushed with 178A at the attachment portion.

*Stipules.*—None.

Inflorescence description:

*Inflorescence type.*—Thyrse compound open pyramidal-shaped panicles on terminals of lateral branches and twigs, flowers are small and non-showy with the pedicels expanding and becoming plumose-villose and showy in mid summer.

*Inflorescence size.*—Average of 21 cm in length and 14 cm in width.

*Rachis.*—Average of 1 cm in length and 0.5 mm in width, average internode length is 1 cm, glabrous and glossy surface, 144A to 144B in color.

*Peduncle.*—15 cm in length, 3 mm in diameter, moderately strong and bendable, glossy and glabrous surface, 144A in color.

*Pedicels.*—2 types of pedicels are present, one develops flowers, the other is flowerless and develops silky hair-like pedicels, flower; 5 mm in length and 0.4 mm in width, 144A on color, surface is slightly glossy and glabrous, held in multiple angles, flowerless; 2.5 cm in length, 0.4 mm in diameter, fine and round in shape, tip has a round shaped ball that has a matte surface, 0.4 mm in diamter, 158A in color, pedicels held in multiple angles, color; 144A, top 184A, surface is glossy and densely covered with soft, fine, long woolly pubescence 0.7 mm in length, 159B in color.

*Flower buds.*—Round in shape, 1 mm in depth and diameter, glabrous and matte surface, young buds; 161A in color, before burst; 167A in color.

*Flower fragrance.*—None.

*Lastingness of flowers.*—True flowers are short lived (less than one week) with showy pedicels lasting about one month, persisting into fall.

*Flowers.*—Average of 480 per compound inflorescence, star-shaped, rotate, upright on pedicels, average of 3 mm in diameter and 1 mm in depth.

*Flower petals.*—5, about 1 mm in length and 0.5 mm in width, un-fused and spreading, slightly cupped, elliptic in shape, cuneate base, acute apex, glabrous and matte surfaces, 155A in color.

*Sepals.*—5, 1 mm in length and 0.7 mm in width, fused base, acute apex, surfaces are matte and glabrous, 144A in color.

Reproductive organs:

*Pistils.*—1, minute, style and stigma; not conspicuous, ovary; superior, round in shape, 3-carpelled, glabrous and glossy surface, 1 mm in length and diameter, 144A in color.

*Stamens.*—5, filament; 0.7 mm in length, 144A in color, anther; flattened, 0.4 mm in length, 1A in color.

*Fruit and seed.*—Fruit; average of 50 per inflorescence, flattened and kidney shaped, strong, glabrous and glossy surface, 3 mm in diameter and length, 0.5 mm in depth, young emerging fruit is 185A in color, maturing to 144A in color, seed; 1, 0.5 mm in diameter, 202A in color.

It is claimed:

1. A new and distinct cultivar of *Cotinus* plant named 'Mincolem04' as herein illustrated and described.

* * * * *